United States Patent

Eyal et al.

[11] Patent Number: 5,972,662
[45] Date of Patent: Oct. 26, 1999

[54] PROCESS FOR THE PREPARATION OF ASPARTIC ACID

[75] Inventors: Aharon Eyal, Jerusalem, Israel; Pierre Cami, Languevoisin, France

[73] Assignees: Amylum N.V., Aalst, Belgium; A.E. Stanley Manufacturing Company, Decatur, Ill.

[21] Appl. No.: 09/101,779

[22] PCT Filed: Jan. 21, 1997

[86] PCT No.: PCT/GB97/00176

§ 371 Date: Oct. 13, 1998

§ 102(e) Date: Oct. 13, 1998

[87] PCT Pub. No.: WO97/27312

PCT Pub. Date: Jul. 31, 1997

[30] Foreign Application Priority Data

Jan. 22, 1996 [IL] Israel ......................................... 116849

[51] Int. Cl.$^6$ ........................... C12P 13/20; C07C 229/00
[52] U.S. Cl. ............................................ 435/109; 562/571
[58] Field of Search .............................. 435/109; 562/571

[56] References Cited

U.S. PATENT DOCUMENTS

| | | | |
|---|---|---|---|
| 3,030,276 | 4/1962 | Thompson | 195/36 |
| 4,877,731 | 10/1989 | Ling et al. | 435/142 |
| 5,352,825 | 10/1994 | Felman et al. | 562/580 |

OTHER PUBLICATIONS

R.A. Rhodes et al., "Production of Fumaric Acid by *Rhizopus arrhizus*", vol. 7, pp. 74–80.

K. Hotta et al., "Conversion of Fumaric Acid Fermentation to Aspartic Acid Fermenation by the Association of Rhizopus and Bacteria", J. Ferm. Tech., vol. 51, No. 1, pp. 12–18, 1973.

I. Goldberg et al., "Improved Rate of Fumaric Acid Production by Tweens and Vegetable Oils in *Rhizopus arrhizus*", Biotech. & Bioeng., vol. 27, No. 7, Jul. 1985, pp. 1067–1069.

M. Moresi et al., Optimization of fumaric acid production from potato flour by *Rhizpus arrhizus*, Appl. Micro. Biotech. (1991), 36:335–39.

H. Kautola et al., "Fumaric acid production from xylose by immobilized *Rizopus arrhizus* cells", Appl. Microbiol. Biotech. (1989), 31:448–452.

I.C. Gangl et al., "Economic Comparison of Calcium Fumarate and Sodium Fumarate Production by *Rhizopus arrhizus*", Appl. Biochem. Biotech., vol. 24/25, 1990, pp. 663–677.

*Primary Examiner*—Herbert J. Lilling
*Attorney, Agent, or Firm*—Foley & Lardner

[57] ABSTRACT

The invention provides a process for the preparation of aspartic acid via a fermentation process for the preparation of ammonium fumarate, wherein the pH of the fermentation broth is controlled by the addition of a calcium base to produce a calcium fumarate precipitate, characterized in that ammonium fumarate is produced by separating the precipitated calcium fumarate from the fermentation broth, and reacting the same with a reagent selected from ammonia, ammonium carbonate, ammonia in combination with $CO_2$ and mixtures thereof, to form ammonium fumarate and a co-product selected from calcium carbonate and calcium hydroxide, wherein the energy of indirect neutralization of fumaric acid by ammonia serves as the driving force for the conversion of calcium fumarate to the desired ammonium fumarate product and for the regeneration of a calcium base reagent, and wherein diammonium fumarate is enzymatically converted to ammonium aspartate and acidulated to from aspartic acid.

12 Claims, No Drawings

PROCESS FOR THE PREPARATION OF ASPARTIC ACID

The present invention relates to a process for the production of aspartic acid.

More particularly, the present invention relates to the preparation of aspartic acid via a fermentation process for the preparation of ammonium fumarate.

Aspartic acid is the 2-aminobutanedioic acid, occurring in its L-form in animals and plants. It is a reagent in the production of the artificial sweetener aspartame. L-Aspartic acid is one of the amino acids that is difficult to produce directly by fermentation. Consequently it is produced enzymatically by conversion of diammonium fumarate to ammonium aspartate which is then acidulated.

GB 1 004 218 discloses a process for the production of L-aspartic acid, comprising mixing a strain of *Pseudomonas trifolii* with an aqueous solution of fumaric acid or a fumarate, and ammonia or an ammonium salt, allowing the mixture to stand under neutral or mildly alkaline conditions to allow L-aspartic acid to accumulate therein, and recovering. the L-aspartic acid from the mixture. Preferably diammonium fumarate serves as both the fumarate and the ammonium salt.

Diammonium fumarate is obtained by neutralizing fumaric acid with ammonia. About one half of the total aspartic acid production cost is due to the fumaric acid consumed. Fumaric acid is presently produced by catalytical isomerisation of maleic anhydride or maleic acid produced mostly from benzene. In the early 1940's fumaric acid was made on a commercial scale by Pfizer by fermentation of glucose using a strain of the fungus Rhizopus. Production was stopped when the economically more attractive synthesis from maleic acid was developed.

Since then many improvements to the fermentation were made. U.S. Pat. No. 4,877,731 describes an improved fermentation process for producing carboxylic acids. The improvement comprises growing fungi of the genus Rhizopus in a culture medium under conditions of controlled oxygen availability. Goldberg and Steiglitz (Biotechnology and Bioengineering Vol. 27, 1067–1069 (1985) have found that adding surfactants or vegetable oils increased the rate of fumaric acid accumulation. Other improvements and optimizations were made by Rhodes et. al (Applied Microbiology, 7, 74–80 (1959)), Moresi et. al (Applied Microbiology and Biotechnology, 36, 35–39, 1991), Kautola and Linko (Applied Microbiology and Biotechnology, 31, 448–482 (1989)) and others.

In spite of these improvements fumaric acid is not produced presently by fermentation. This is at least partially due to the complicated and costly process for its recovery from the fermentation broth. In the fermentation, as the pH of the broth drops in consequence of production, the rate of fumaric acid production slows down and eventually ceases. $CaCO_3$ is added as a neutralizing agent to prevent this self-inhibition. Because of its insolubility, $CaCO_3$ offers the advantage of all-at-once addition and therefore eliminates the requirement of a control system for base addition. However, because of the low solubility of calcium fumarate at the fermentation temperature, the product precipitates out of the broth throughout the fermentation. At the end of the fermentation. the broth, containing a slurry of calcium fumarate. is heated to 160° C. in a reactor and is acidified to pH 1.0 by $H_2SO_4$. At this temperature, both calcium fumarate and fumaric acid are soluble, but calcium sulfate precipitates out of solution and is filtered off. Fumaric acid crystals are recovered by cooling the filtrate.

The overall process thus consumes $CaCO_3$ and $H_2SO_4$ as reagents produces gypsum as an undesired by-product, consumes energy for the reaction at high temperature and requires handling an acidic solution at very high temperatures. All these elements add to the cost of fumaric acid production through fermentation and render fumaric acid, produced by fermentation, an unfavorable reagent for aspartic acid manufacture.

Conversion of fumaric acid fermentation to aspartic acid fermentation by the combination of Rhizopus and bacteria (Proteus vulgaris) was attempted, but the results were not favorable (Hotta and Takao, Hakko Kogaku Zasshi 51, 12–18 (1973)). An alternative could have been neutralization of the fermentation by ammonia to directly form ammonium fumarate for further purification or direct conversion to aspartic acid. That is however not attainable as explained by Goldberg and Steigliz: "The key point in fumaric acid accumulation is adding a limiting amount of nitrogen (e.g. urea) as cells starved for nitrogen produce fumaric acid and not biomass from glucose." Another suggestion was to use $Na_2CO_3$ as the neutralizing base to form sodium fumarate in the fermentation broth and recovering the fumaric acid therefrom by acidulation (Gangl et. al, Applied Biochemistry and Biotechnology 24/25, 663–677, (1990)). However formation of a soluble fumarate salt in the fermentation liquor has a negative effect on production.

With this state of the art in mind, there is now provided, according to the present invention, a process for the preparation of aspartic acid via a fermentation process for the preparation of ammonium fumarate, wherein the pH of the fermentation broth is controlled by the addition of a calcium base to produce a calcium fumarate precipitate, characterized in that ammonium fumarate is produced by separating said precipitated calcium fumarate from said fermentation broth, and reacting the same with a reagent selected from ammonia, ammonium carbonate, ammonia in combination with $CO_2$ and mixtures thereof, to form ammonium fumarate and a co-product selected from calcium carbonate and calcium hydroxide, wherein the energy of indirect neutralization of fumaric acid by ammonia serves as the driving force for the conversion of calcium fumarate to the desired ammonium fumarate product and the regeneration of a calcium base reagent, and diammonium fumarate is enzymatically converted to ammonium aspartate and acidulated to form aspartic acid.

In preferred embodiments of the present invention said calcium base co-product is recycled to the fermentation broth.

Preferably said precipitated calcium fumarate from said fermentation broth is subjected to purification before reaction with said reagent.

In especially preferred embodiments, said precipitated calcium fumarate is recrystallized before said reaction.

U.S. Pat. No. 5,352,825 teaches a method for the recovery of organic acid salt from an impure process stream, comprising the steps of:

a. obtaining a solution of an organic acid salt of interest, concentrated to within about ten percent of the saturation point;

b. adding a sufficient amount of crystallizing base to the concentrated solution of the organic acid salt to produce crystals of the salt; and (c) separating the crystallized organic acid salt from mother liquor. The "crystallizing base" added in step b causes crystallization of the organic acid salt present already in the impure stream or produced therein by adding a "neutralizing base". The "crystallizing base"

need not be consistent with that of the "neutralizing base". Thus, Example 3 of the patent describes production of trisodium citrate from a solution containing it by adding ammonia as a crystallizing base.

In contrast to U.S. Pat. No. 5,352,825, in the new process the added reagent does not facilitate the production of the calcium fumarate present in the fermentation broth, but causes its conversion to ammonium fumarate.

Thomsen (U.S. Pat. No. 3,030,276) describes the manufacture of fumaric acid from lignified cellulose which comprises; digesting said lignified cellulose with a solution of caustic soda under the conventional limitations as to alkali concentration, time and. temperature, until substantially all the non-cellulose portion shall have been dissolved; separating the spent cooking liquor for subsequent conventional regeneration and recycling to said digestion step from the cellulose residual and saccharifying the latter with dilute sulphuric acid under the conventional limitations as-to acid concentration, time and temperature; commingling the resultant sugar solution with a recirculated excess of calcium carbonate produced in a subsequent step and with a microorganism suitable for the conversion of sugar into fumaric acid; commingling the resultant mixture of calcium sulphate, fumarate and carbonate with sufficient carbonated ammonia to decompose all such sulphate and fumarate forming calcium carbonate and sulphate and fumarate of ammonium; separating and recycling such calcium carbonate and evaporating the resultant solution to substantial saturation and acidifying said solution of ammonium sulphate and ammonium fumarate with the stoichiometric amount of sulphuric acid to decompose all resident fumarate and crystallizing out the liberated fumaric acid from the residual solution of ammonium sulphate.

While a conversion of calcium fumarate and cabonated ammonia to ammonium fumarate and calcium carbonate is described in said patent, it does not teach the economic formation of ammonium fumarate for aspartic acid production.

Firstly, according to Thomsen the production of fumaric acid as the sole product is not economic and should be combined with the production of urea. "Owing to its cost, fumaric acid is as yet of little importance . . . Urea and its production is too well known . . . but it is the aim and object of my process to link the simultaneous production of both in such a manner that the discard from one series of steps supplements the need of the other series, eliminating all waste effort and cheapening the cost of both. The best way to evaluate said linkages . . . the chemical reactions involved are old, only the combinations being new. That, however, is the important part for it is upon such that the economy, hence the value of my process rests."

Secondly, the conversion of calcium fumarate to calcium carbonate and ammonium fumarate is made in U.S. Pat. No. 3,030,276, in the presence of gypsum and ammonium sulfate "comingling the resultant mixture of calcium sulfate, fumarate and carbonate with sufficient carbonated ammonia to decompose all such sulfate and fumarate forming calcium carbonate and sulfate and fumarate of ammonium." Thomsen does not teach that efficient conversion can be achieved without the facilitating effect of salting out by the presence of other salts. This could be of particular importance in the current case where one of the reagents and one of the products are solids and the reaction kinetics could be slow. In fact, no details of the reaction conditions, such as temperature, pressure and what is "sufficient carbonated ammonia", are given and no claims are made as to the degree of the conversion and as to the product concentration. No examples are provided.

Furthermore, Thomsen does not teach the recovery of ammonium fumarate pure enough and concentrated enough for conversion into aspartic acid. In fact, his process requires concentration of the ammonium fumarate containing solution and purification through the addition of sulfuric acid and crystallization of fumaric acid "evaporating the resultant solution to substantial saturation and acidifying said solution of ammonium sulfate and ammonium fumarate with the stoichiometric amount of sulfuric acid to decompose all resident fumarate and crystallizing out the liberated fumaric acid from the residual solution of ammonium fumarate". One could indeed follow this process and react the separated fumaric acid with ammonia to form ammonium fumarate for conversion to aspartic acid. It would, however, result in the production of at least an equivalent amount of ammonium sulfate which is a waste or a low grade fertilizer.

Considering the proposed process for reacting calcium fumarate with a reagent selected from ammonia, ammonium carbonate, ammonia in combination with $CO_2$ and mixtures thereof and based on the teachings of the prior art, one would expect several difficulties. The solubility of calcium fumarate at about ambient temperature, is low (2.11 w/v at 30° C.). Reactions of solid reagents are slow in many cases. An additional degree of complication is added by the fact that one of the reaction products, $CaCO_3$, is insoluble, which adds to the foreseen difficulties in contacting the reagents for a rapid reaction. Another potential difficulty is the possibility of $CaCO_3$ precipitation on the surface of calcium fumarate crystals, further slowing their interaction with the reagent.

The calcium fumarate reaction with sulfuric acid to form fumaric acid and gypsum seem to face a similar problem. There it was solved by conducting the reaction at 160° C., a temperature high enough to solubilize the calcium fumarate. Adopting a similar solution to the present case could be difficult. Since ammonium carbonate decomposes at these elevated temperatures, and since the solubility of ammonia, and particularly that of $CO_2$ in the reaction medium decreases, the reaction rate is expected to slow. A possible solution is operating the reaction under high pressure, but that would add significantly to the cost of the production.

Another element of high importance is that of pH adjustment to the contradictory requirements of the reaction. The preferred product for the conversion to aspartic acid is diammonium fumarate. This allows operating the reaction at high ammonium concentrations which facilitates the reaction. An excess of ammonia could be considered in order to assist in maintaining the $CO_2$ or $CO_3^{2-}$ content of the reaction mixture. The possible difficulties are the need of removal of an excess of ammonia from the reaction mixture and the possible precipitation of $Ca(OH)_2$ rather than $CaCO_3$ as a by-product at high pH. The process of this invention could use $Ca(OH)_2$ as the neutralizing agent and reform it from calcium fumarate. $CaCO_3$ is, however, a preferred neutralizing agent in the fermentation as it introduces $CO_2$. Such $CO_2$ introduction is needed to increase the fermentation yield.

Alternately one could design the process and the reagent ratio to form monoammonium fumarate which would be converted later to aspartic acid after the addition of ammonia. However, the dissociation constants of fumaric acid should be noted: $pKa_1=3.03$ and $pKa_2=4.44$. The pH of a reaction solution comprising mono ammonium fumarate would be lower than 4. The dissociation constants of carbonic acid are high: $pKa_1=6.37$ and $pKa_2=10.25$. Calcium carbonate precipitation at pH of about 4 is very difficult and even at the pH of diammonium fumarate, about 5, would not precipitate easily high $CO_2$ pressure was found in many cases to assist in precipitation of bicarbonate salts (particularly $NaHCO_3$), but is not desired in the present case.

Another aspect of importance is that of product concentration. This bioconversion should be fed with as concentrated as possible solution of diammonium fumarate for efficiency and for reducing losses in the aspartic acid recovery. According to the prior art one would expect that a significant amount of water would be needed in the reaction to maintain a sufficient amount of calcium fumarate in solution. This amount of water would end up in the product ammonium fumarate and dilute it.

The fermentation of cabohydrates to fumaric acid (fumarate at the fermentation pH) is usually not very selective. Typically only about 80% of the total carboxylate formed is fumarate, the rest being typically maleate, succinate and alpha ketogluterate. In addition, the fermentation liquor contains other organic fermentation products such as glycerol. Those fermentation by-products, as well as other impurities, such as non-utilized carbohydrates, mineral cations and anions and nitrogen containing compounds, may cause difficulties in the next step of bioconverting ammonium fumarate to ammonium aspartate. Even if not, these impurities could end up in the ammonium aspartate formed and cause major difficulties in the recovery of pure aspartic acid at high yields.

With this background it was surprising to find that the reaction of calcium fumarate to convert it to ammonium fumarate and calcium carbonate can be conducted under favorable conditions:

a. The amount of water needed in the reaction is limited and ammonium fumarate can be obtained at a nearly saturated solution.

b. The reaction yield at about ambient temperature is nearly 100% and elevated temperatures are not required. In fact, high temperatures reduced the reaction yield.

c. High $CO_2$ pressures are not required and practically full conversion is obtained at $CO_2$ pressure of less than 5 and preferably at a $CO_2$ pressure of less than 2 atmospheres.

d. The calcium carbonate that forms does not coat the calcium fumarate and is obtained in clean, easy to separate crystals.

Thus it will be realized that in counterdistinction to Thomsen, the present invention does not require the production of fumaric acid through the wasteful addition of sulphuric acid, and instead is based on the formation of ammonium fumarate. Most of the fermentation by-products are removed in the process and the ammonium fumerate formed is pure enough for direct conversion to ammonium aspartate.

The reagent for the reaction is selected from ammonia, ammonium carbonate, ammonia in combination with $CO_2$ and mixtures thereof. The amount of ammonia or ammonium ion in the reagent is preferably at least one mole and more preferably about two moles per mole of calcium fumarate. Even more preferred is an excess of about 10% over the 2:1 molar ratio since the bioconversion to aspartic acid is facilitated by an excess of ammonia. It was found that when the reagent is ammonium carbonate, the yield and the rate of the reaction are improved by adding to the reaction medium a small amount of ammonia to adjust the pH there to about 10–11 prior to the addition of ammonium carbonate.

The amount of $CO_2$ or $CO_3^{2-}$ in the reagent is preferably about one mole per mole of calcium fumarate. It could be introduced as a gaseous $CO_2$ or as ammonium carbonate or bicarbonate. In both cases the reaction is preferably performed in a closed system to avoid $CO_2$ losses. In cases of gaseous $CO_2$ addition the pressure in the reactor should stay below 5 atmospheres.

Gaseous ammonia or aqueous ammonia or ammonium carbonate solutions can be used. The amount of water introduced with the reagent is adjusted to a level that will not exceed the level equivalent to final fumarate concentration of about 50% of saturation. Preferably the amount of water is such that the final fumarate concentration is at least 80% of saturation.

The reaction temperature is preferably below 80°C. and even more preferred below 50° C.

In a preferred embodiment the calcium fumarate is separated from the fermentation liquor, e.g., by filtration, and washed with water or with an aqueous solution from a previous step.

One can also take advantage of the low solubility of calcium fumarate at low temperature and enhanced solubility at high temperatures. This provides for a preliminary purification of the calcium fumarate formed in the fermentation by recrystallization. This recrystallization serves to remove the biomass and a significant amount of the impurities.

If needed, the ammonium fumarate formed in the reaction, can be further purified by converting it back to water immiscible calcium fumarate (e.g. by reacting it with calcium hydroxide or carbonate) and washing away the water soluble impurities.

Preferably the calcium base (carbonate or hydroxide) formed as a by-product is separated from the ammonium fumarate and reused as a neutralizing agent in carbohydrate fermentation to fumarate. Preferably the calcium base is calcined prior to the reuse, whereby biomass left in it is removed. In a most preferred embodiment the calcined calcium base is quenched in water or in an aqueous solution and kept suspended in it until used. This suspension in water helps in removal of ashes left from biomass burning and other ashes left from the fermentation step.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

15.4 g of solid calcium fumarate were mixed in a beaker of water and a few drops of 25% ammonia were added to adjust the pH of the solution to about 10. Most of the calcium fumarate remained undissolved. 10.6 g of solid ammonium carbonate was added into the beaker that was held at ambient temperature and was mixed strongly. After one hour of mixing, the beaker contained a large amount of solids. After filtration and washing the solid was analyzed. The analysis showed that it was calcium carbonate. The filtrate was analyzed for fumarate anion. The fumarate concentration in it was 0.87 mol/kg (about 13% w/w of diammonium fumarate), indicating a substantially complete conversion.

The filtrate was then converted enzymatically to ammonium asparate and then acidulated with an equivalent amount of sulfuric acid to precipitate out aspartic acid.

EXAMPLE 2

Solid ammonium carbonate was added gradually into 50 g mixed suspension containing about 10% calcium fumarate until the carbonate to fumarate molar ratio reached 1.1:1. The initial temperature of the suspension was 22° C. After the addition of the carbonate the mixing was continued for additional 30 minutes without any heating. Then the solids were filtered and washed, the filtrate was combined with the wash water and the combined solution was analyzed for fumarate 99.5% conversion was found.

EXAMPLE 3

50 g. of a suspension containing about 10% calcium fumarate were introduced into a pressure vessel. Solid ammonium carbonate was added in one portion and the vessel was closed. The amount of ammonium carbonate was adjusted to a carbonate fumarate molar ratio of 1.1:1. Strong mixing was applied for 2 hours. No heating was applied. In the first 5–10 minutes a pressure rise was observed. Then it decreased back to one atmosphere. The pH of the final solution was about 8. Its fumarate content showed 95% conversion.

EXAMPLE 4

5 Kg. of fermentation broth analyzed and was found to contain: 329 g (2.84 mole) fumarate, 39.5 g (0.29 mole) maleate, 24 g (0.20 mole) succinate, 20.5 g (0.14 mole) alpha ketoglutarate and 76.5 g (0.83 mole) glycerol. The broth was filtered and the solids were washed with water to form 1.42 Kg of wet cake containing: 283 g (23.44 mole) fumarate, 4.2 g (0.031 mole) maleate, 8.8 g (0.074 mole) succinate, <9 g (<0.062 mole) alpha ketoglutarate and <3 g (<0.032 mole) glycerol.

The 1.42 Kg. wet cake was re-suspended in 1.5 Kg de-ionized water at 30° C. and 344 g of a 33% ammonia solution was added. Gaseous CO2 was then bubbled through the suspension until the pH was 8.7. After cooling the ambient temperature the suspension was filtered and the cake was washed with 1.2 Kg. water. The wash water was combined with the filtrate. The composition of the combined solution was 257 g (2.21 mole) fumarate (>90% conversion), 2.2 g. (0.016 mole) maleate, 8.2 g. (0.069 mole) succinate, 0.4 g (0.003 mole) alpha ketoglutarate 0.18 g (0.0045 mole) calcium and 90 g (5 mole) ammonia.

These results show that high conversion yields can be combined with a substantial purification of the fumarate. The proportion of the fumarate in the total fermentation products increased from 67% in the broth to 96% in the product ammonium fumarate.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A process for the preparation of aspartic acid via a fermentation process for the preparation of ammonium fumarate, wherein the pH of the fermentation broth is controlled by the addition of a calcium base to produce a calcium fumarate precipitate, characterised in that ammonium fumarate is produced by separating said precipitated calcium fumarate from said fermentation broth, and reacting said precipitate with a reagent selected from ammonia, ammonium carbonate, ammonia in combination with $CO_2$ and mixtures thereof, to form ammonium fumarate solution and a co-product selected from calcium carbonate and calcium hydroxide, wherein the energy of indirect neutralisation of fumaric acid by ammonia serves as the driving force for the conversion of calcium fumarate to the desired ammonium fumarate product with a conversion yield of at least 90% and for the regeneration of a calcium base reagent, and wherein said ammonium fumarate product is enzymatically converted to ammonium aspartate and acidulated to form aspartic acid.

2. A fermentation process according to claim 1, wherein said calcium base co-product is recycled to the fermentation broth.

3. A fermentation process according to claim 1, wherein the amount of water introduced with said reagent is controlled such that it will not exceed the level equivalent to final fumarate concentration of about 50% of saturation.

4. A fermentation process according to claim 3, wherein the amount of water introduced with said reagent is controlled such that the final fumarate concentration is at least 80% of saturation.

5. A fermentation process according to claim 1, wherein said precipitated calcium fumarate from said fermentation broth is subjected to purification before reaction with said reagent.

6. A fermentation process according to claim 5, wherein said precipitated calcium fumarate from said fermentation broth is recrystallized before reaction with said reagent.

7. A fermentation process according to claim 1, wherein said precipitated calcium fumarate is first reacted with ammonia in an aqueous medium to raise the pH of the reaction medium to between about 10 and 11, and then ammonium carbonate is added thereto.

8. A fermentation process according to claim 1, wherein the amount of $CO_2$ in said reagent is about 1 mole per mole of calcium fumarate.

9. A fermentation process according to claim 1, wherein said reaction is carried out at a temperature below 80° C.

10. A fermentation process according to claim 1, wherein said reaction is carried out at a temperature below 50° C.

11. A fermentation process according to claim 1, wherein said reaction is carried out using gaseous $CO_2$ and is performed at a pressure below 5 atmospheres.

12. A fermentation process according to claim 1, wherein said ammonium fumarate product is obtained at a purity of about 96% of the total carboxylates formed.

* * * * *